US011352651B2

(12) United States Patent
Diehl et al.

(10) Patent No.: US 11,352,651 B2
(45) Date of Patent: Jun. 7, 2022

(54) METHOD OF ISOLATING LIPIDS FROM A LIPIDS CONTAINING BIOMASS

(71) Applicants: EVONIK OPERATIONS GMBH, Essen (DE); DSM IP ASSETS B.V., TE Heerlen (NL)

(72) Inventors: Michael Diehl, Frankfurt (DE); Xiao Daniel Dong, Woodstock, MD (US); Annika Hartmann, Karlstein am Main (DE); Martin Heining, Karlstein am Main (DE); Michael Benjamin Johnson, Baltimore, MD (US); Jochen Lebert, Glattbach (DE); Neil Francis Leininger, Winchester, KY (US); Kirt Lyvell Matthews, Sr., Fort Mill, SC (US); Mark Edward Nejako, II, Woodbine, MD (US); Holger Pfeifer, Wulfen (DE); Christian Rabe, Grossostheim (DE); Shannon Elizabeth Ethier Resop, Olney, MD (US); Ginger Marie Shank, Winchester, KY (US); Vinod Tarwade, Ellicott City, MD (US); David Allen Tinsley, Versailles, KY (US)

(73) Assignees: Evonik Operations GmbH, Essen (DE); DSM IP Assets B.V., TE Heerlen (NL)

(*) Notice: Subject to any disclaimer, the term of this patent is extended or adjusted under 35 U.S.C. 154(b) by 0 days.

(21) Appl. No.: 16/473,805

(22) PCT Filed: Dec. 20, 2017

(86) PCT No.: PCT/EP2017/083712
§ 371 (c)(1),
(2) Date: Jun. 26, 2019

(87) PCT Pub. No.: WO2018/122057
PCT Pub. Date: Jul. 5, 2018

(65) Prior Publication Data
US 2019/0323043 A1 Oct. 24, 2019

Related U.S. Application Data

(60) Provisional application No. 62/439,354, filed on Dec. 27, 2016.

(30) Foreign Application Priority Data

Feb. 28, 2017 (EP) .................................... 17158286

(51) Int. Cl.
*C12P 7/64* (2022.01)
*C11B 1/10* (2006.01)
*C12P 7/6463* (2022.01)

(52) U.S. Cl.
CPC .............. *C12P 7/6463* (2013.01); *C11B 1/10* (2013.01)

(58) Field of Classification Search
None
See application file for complete search history.

(56) References Cited

U.S. PATENT DOCUMENTS

| | | |
|---|---|---|
| 5,622,710 A | 4/1997 | Binder et al. |
| 6,166,230 A | 12/2000 | Bijl et al. |
| 6,166,231 A | 12/2000 | Hoeksema |
| 6,255,505 B1 | 7/2001 | Bijl et al. |
| 6,410,281 B1 | 6/2002 | Barclay |
| 6,410,282 B1 | 6/2002 | Kumar et al. |
| 6,441,208 B2 | 8/2002 | Bijl et al. |
| 6,727,373 B2 | 4/2004 | Bijl et al. |
| 6,750,048 B2 | 6/2004 | Ruecker et al. |
| 6,977,167 B2 | 12/2005 | Barclay |
| 7,005,280 B2 | 2/2006 | Barclay |
| 7,011,962 B2 | 3/2006 | Barclay |
| 7,041,485 B2 | 4/2006 | Bouarab et al. |
| 7,163,811 B2 | 1/2007 | Behrens et al. |
| 7,252,979 B2 | 8/2007 | Behrens et al. |
| 7,351,558 B2 | 4/2008 | Ruecker et al. |
| 7,419,596 B2 | 9/2008 | Dueppen et al. |
| 7,431,952 B2 | 10/2008 | Bijl et al. |
| 7,470,527 B2 | 12/2008 | Streekstra et al. |

(Continued)

FOREIGN PATENT DOCUMENTS

| | | |
|---|---|---|
| AU | 2011226731 | 9/2011 |
| EP | 1 178 118 | 2/2000 |

(Continued)

OTHER PUBLICATIONS

International Search Report for corresponding international application PCT/EP2017/083712 filed Dec. 20, 2017.
Written Opinion of the International Searching Authority for corresponding international application PCT/EP2017/083712 filed Dec. 20, 2017.
International Preliminary Report on Patentability for corresponding international application PCT/EP2017/083712 filed Dec. 20, 2017.
European Search Report and Search Opinion for counterpart European application EP 17 15 8286 filed Feb. 28, 2017.
International Search Report for PCT/EP2017/067570, filed Jul. 12, 2017; for copending U.S. Appl. No. 16/317,249.

(Continued)

*Primary Examiner* — Nghi V Nguyen
(74) *Attorney, Agent, or Firm* — Law Office of: Michael A. Sanzo, LLC

(57) ABSTRACT

The invention relates to the isolation of polyunsaturated fatty acids (PUFAs) from a lipids containing biomass. The main characteristics of the method are that a suspension of cells containing PUFAs is obtained and the cells are optionally lysed. The suspension is concentrated and then incubated for at least an hour at a controlled temperature while adding a specific range of base equivalents to biomass and maintaining a moderate pH. The isolation of lipid may be performed in the absence of organic solvents and without the addition of salt.

20 Claims, No Drawings

(56) References Cited

U.S. PATENT DOCUMENTS

| | | |
|---|---|---|
| 7,566,570 B2 | 7/2009 | Abril |
| 7,579,174 B2 | 8/2009 | Bailey et al. |
| 7,662,598 B2 | 2/2010 | Ruecker et al. |
| 7,732,170 B2 | 6/2010 | Bailey et al. |
| 7,776,375 B2 | 8/2010 | Bertholet et al. |
| 7,781,193 B2 | 8/2010 | Ruecker et al. |
| 7,968,737 B2 | 6/2011 | Kawashima et al. |
| 8,217,151 B2 | 7/2012 | Schaap et al. |
| 8,415,506 B2 | 4/2013 | Waibel et al. |
| 9,023,625 B2 | 5/2015 | Pottathil et al. |
| 9,045,785 B2 | 6/2015 | Pfeifer, III |
| 9,896,642 B2 | 2/2018 | Wittenberg et al. |
| 10,342,772 B2 | 7/2019 | Barker et al. |
| 10,364,207 B2 | 7/2019 | Barker et al. |
| 10,472,316 B2 | 11/2019 | McClements et al. |
| 10,531,679 B2 | 1/2020 | Rudinger et al. |
| 10,619,175 B2 | 4/2020 | Rabe et al. |
| 10,842,174 B2 | 11/2020 | Durhuus et al. |
| 11,124,736 B2 | 9/2021 | Triplett et al. |
| 2003/0143659 A1 | 7/2003 | Bijl et al. |
| 2007/0003686 A1 | 1/2007 | Fichtali et al. |
| 2008/0032360 A1 | 2/2008 | Bailey et al. |
| 2008/0032365 A1 | 2/2008 | Bailey et al. |
| 2008/0166780 A1 | 7/2008 | Barclay |
| 2008/0199923 A1 | 8/2008 | Barclay |
| 2008/0233239 A1 | 9/2008 | Avramis et al. |
| 2008/0305531 A1 | 12/2008 | Lam et al. |
| 2009/0326267 A1 | 12/2009 | Bijl et al. |
| 2010/0227042 A1 | 9/2010 | Penet et al. |
| 2011/0091947 A1 | 4/2011 | Kim et al. |
| 2011/0098356 A1 | 4/2011 | Leininger et al. |
| 2011/0124034 A1* | 5/2011 | Kuehnle ............... C10L 1/02 435/29 |
| 2011/0201683 A1 | 8/2011 | Bezelgues et al. |
| 2011/0295028 A1 | 12/2011 | Cherinko et al. |
| 2012/0016145 A1* | 1/2012 | D'Addario ............. C11C 3/003 554/21 |
| 2012/0059180 A1 | 3/2012 | Dueppen et al. |
| 2013/0065282 A1 | 3/2013 | Tran et al. |
| 2013/0102802 A1 | 4/2013 | Sathish et al. |
| 2013/0172590 A1 | 7/2013 | Pfeifer, III |
| 2014/0096437 A1 | 4/2014 | Crowell et al. |
| 2015/0104557 A1 | 4/2015 | Rusing et al. |
| 2015/0176042 A1 | 6/2015 | Dennis et al. |
| 2016/0183565 A1 | 6/2016 | Rudinger et al. |
| 2016/0249642 A1 | 9/2016 | Rabe et al. |
| 2016/0289592 A1 | 10/2016 | Massetti et al. |
| 2016/0319218 A1 | 11/2016 | Leininger et al. |
| 2017/0137742 A1* | 5/2017 | Heiska .................. C10L 9/086 |
| 2017/0290356 A1 | 10/2017 | Silva et al. |
| 2017/0295823 A1 | 10/2017 | Rabe et al. |
| 2017/0295824 A1 | 10/2017 | Priefert et al. |
| 2017/0298318 A1 | 10/2017 | Rabe et al. |
| 2017/0303561 A1 | 10/2017 | Durhuus et al. |
| 2017/0306365 A1 | 10/2017 | Rabe et al. |
| 2018/0071658 A1 | 3/2018 | Hale et al. |
| 2018/0192669 A1 | 7/2018 | Wilson |
| 2018/0200644 A1 | 7/2018 | Lewis |
| 2019/0249108 A1 | 8/2019 | Cherinko |
| 2019/0300818 A1 | 10/2019 | Bärz et al. |
| 2019/0390135 A1 | 12/2019 | Leininger et al. |
| 2020/0015500 A1 | 1/2020 | De Vriendt |
| 2020/0231896 A1 | 7/2020 | Bahl et al. |
| 2020/0231898 A1 | 7/2020 | Bärz, et al. |
| 2020/0339498 A1 | 10/2020 | Heining et al. |
| 2020/0362373 A1 | 11/2020 | Leininger et al. |
| 2020/0383353 A1 | 12/2020 | Wilson et al. |
| 2020/0404938 A1 | 12/2020 | Heining et al. |
| 2021/0017467 A1 | 1/2021 | Adugna et al. |
| 2021/0024966 A1 | 1/2021 | Heining et al. |
| 2021/0163842 A1 | 6/2021 | Heining et al. |
| 2021/0171991 A1 | 6/2021 | Burja et al. |
| 2021/0207056 A1 | 7/2021 | Heining et al. |
| 2021/0386095 A1 | 12/2021 | Erickson et al. |

FOREIGN PATENT DOCUMENTS

| | | | |
|---|---|---|---|
| EP | 1 252 324 | 10/2020 | |
| JP | H08 275793 | 10/1996 | |
| SU | 1446142 | 12/1988 | |
| WO | WO 91/07498 | 4/1991 | |
| WO | WO 94/08467 | 4/1994 | |
| WO | WO 97/36996 | 10/1997 | |
| WO | WO 97/37032 | 10/1997 | |
| WO | WO 01/53512 | 7/2001 | |
| WO | WO 01/54510 | 8/2001 | |
| WO | WO 2011/153246 | 12/2011 | |
| WO | WO-2011153246 A2 * | 12/2011 | ............... C11B 1/10 |
| WO | WO 2012/109642 | 8/2012 | |
| WO | WO 2014/122087 | 8/2014 | |
| WO | WO 2014/122092 | 8/2014 | |
| WO | WO 2015/059696 | 6/2015 | |
| WO | WO 2015/095688 | 6/2015 | |
| WO | WO 2015/095693 | 6/2015 | |
| WO | WO 2015/095694 | 6/2015 | |
| WO | WO 2018/011275 | 1/2018 | |
| WO | WO 2018/011286 | 1/2018 | |
| WO | WO 2018/013670 | 1/2018 | |
| WO | WO 2019/032880 | 2/2019 | |
| WO | WO 2019/048327 | 3/2019 | |
| WO | WO 2019/063669 | 4/2019 | |
| WO | WO 2019/121752 | 6/2019 | |
| WO | WO 2019/122030 | 6/2019 | |
| WO | WO 2019/122031 | 6/2019 | |
| WO | WO 2019/191544 | 10/2019 | |
| WO | WO 2019/191545 | 10/2019 | |
| WO | WO 2019/219396 | 11/2019 | |
| WO | WO 2019/219443 | 11/2019 | |
| WO | WO 2020/036814 | 2/2020 | |
| WO | WO 2020/094750 | 5/2020 | |
| WO | WO 2020/094751 | 5/2020 | |
| WO | WO 2020/109472 | 6/2020 | |
| WO | WO 2020/123965 | 6/2020 | |

OTHER PUBLICATIONS

Written Opinion of the International Searching Authority for PCT/EP2017/067570, filed Jul. 12, 2017; for copending U.S. Appl. No. 16/317,249.
International Preliminary Report on Patentability for PCT/EP2017/067570, filed Jul. 12, 2017; for copending U.S. Appl. No. 16/317,249.
International Search Report for PCT/EP2017/067585, filed Jul. 12, 2017; for copending U.S. Appl. No. 16/317,305.
Written Opinion of the International Searching Authority for PCT/EP2017/067585, filed Jul. 12, 2017; for copending U.S. Appl. No. 16/317,305.
International Preliminary Report on Patentability for PCT/EP2017/067585, filed Jul. 12, 2017; for copending U.S. Appl. No. 16/317,305.
U.S. Appl. No. 14/904,665, filed Jan. 12, 2016, Rudinger, et al.
U.S. Appl. No. 15/027,429, filed Apr. 5, 2016, Rabe, et al.
U.S. Appl. No. 15/516,022, filed Mar. 31, 2017, Rabe, et al.
U.S. Appl. No. 15/516,023, filed Mar. 31, 2017, Silva, et al.
U.S. Appl. No. 15/516,024, filed Mar. 31, 2017, Priefert, et al.
U.S. Appl. No. 15/516,038, filed Mar. 31, 2017, Rabe, et al.
U.S. Appl. No. 15/516,044, filed Mar. 31, 2017, Rabe, et al.
U.S. Appl. No. 15/516,058, filed Mar. 31, 2017, Durhuus, et al.
U.S. Appl. No. 16/317,249, filed Jan. 11, 2019, Bärz, et al.
U.S. Appl. No. 16/317,305, filed Jan. 11, 2019, Bärz, et al.
International Search Report for PCT/EP2018/073323, filed Aug. 30, 2018; for copending U.S. Appl. No. 16/644,443.
Written Opinion of the International Searching Authority PCT/EP2018/073323, filed Aug. 30, 2018; for copending U.S. Appl. No. 16/644,443.
U.S. Appl. No. 16/639,529, filed Feb. 14, 2020, Burja.
U.S. Appl. No. 16/644,443, filed Mar. 4, 2020, Bahl.
Restriction Requirement for copending U.S. Appl. No. 16/317,305, dated May 19, 2020.
Response to Restriction Requirement for copending U.S. Appl. No. 16/317,305, filed Jul. 20, 2020.

(56) References Cited

OTHER PUBLICATIONS

Restriction Requirement for copending U.S. Appl. No. 16/317,249, dated Jun. 24, 2020.
Response to Restriction Requirement for copending U.S. Appl. No. 16/317,249, filed Aug. 24, 2020.
Office Action for copending U.S. Appl. No. 16/317,305, mailed dated Aug. 13, 2020.
International Preliminary Report on Patentability for international application PCT/EP2018/073323 filed Aug. 30, 2018, corresponding to copending U.S. Appl. No. 16/644,443.
U.S. Appl. No. 15/315,094, filed Nov. 30, 2016, US-2018/0192669, Jul. 12, 2018, Wilson.
U.S. Appl. No. 16/309,632, filed Dec. 13, 2018, US-2019/0249108, Aug. 15, 2019, Cherinko.
European Search Report and Search Opinion for European application EP 17 19 6348 filed Oct. 13, 2017; counterpart of copending U.S. Appl. No. 16/644,443.
International Search Report for PCT/EP2018/085606, filed Dec. 18, 2018; for copending U.S. Appl. No. 16/956,453.
Written Opinion of the International Searching Authority for PCT/EP2018/085606, filed Dec. 18, 2018; for copending U.S. Appl. No. 16/956,453.
International Preliminary Report on Patentability for PCT/EP2018/085606, filed Dec. 18, 2018; for copending U.S. Appl. No. 16/956,453.
European Search Report and Search Opinion for European application EP 18 15 6840 filed Feb. 15, 2018, counterpart of copending U.S. Appl. No. 16/956,453.
Hu, et al., "A review of recent developments of pre-treatment technologies and hydrothermal liquefaction of microalgae for bio-crude oil production," *Renewable and Sustainable Energy Reviews* 101:476-492 (2019).
U.S. Appl. No. 16/956,453, filed Jun. 19, 2020, Heining.
International Search Report for PCT/EP2019/061244 filed May 2, 2019, for copending U.S. Appl. No. 17/055,083.
Written Opinion of the International Searching Authority for PCT/EP2019/061244 filed May 2, 2019, for copending U.S. Appl. No. 17/055,083.
International Preliminary Report on Patentability for PCT/EP2019/061244 filed May 2, 2019, for copending U.S. Appl. No. 17/055,083.
International Search Report for PCT/EP2019/061629 filed May 7, 2019, for copending U.S. Appl. No. 17/055,047.
Written Opinion of the International Searching Authority for PCT/EP2019/061629 filed May 7, 2019, for copending U.S. Appl. No. 17/055,047.
International Preliminary Report on Patentability for PCT/EP2019/061629 filed May 7, 2019, for copending U.S. Appl. No. 17/055,047.
Non Final Office Action for copending U.S. Appl. No. 16/317,249, dated Dec. 7, 2020.
Response to Office Action for copending U.S. Appl. No. 16/317,305, filed Dec. 11, 2020.
U.S. Appl. No. 17/055,047, filed Nov. 12, 2020, Heining.
U.S. Appl. No. 17/055,083, filed Nov. 12, 2020, Heining.
Non Final Office Action for copending U.S. Appl. No. 16/956,453, dated Aug. 2, 2021.
Amendment & Response to Office Action for copending U.S. Appl. No. 16/317,305, filed Sep. 30, 2021.
Final Rejection for copending U.S. Appl. No. 16/317,305, dated Oct. 12, 2021.
Request for Continued Examination for for copending U.S. Appl. No. 16/317,249, filed Nov. 30, 2021.
Amendment & Response to Accompany RCE for copending U.S. Appl. No. 16/317,249, filed Nov. 30, 2021.
Amendment & Response to Office Action for copending U.S. Appl. No. 16/956,453, filed Dec. 2, 2021.
Response to Restriction Requirement for copending U.S. Appl. No. 16/956,453, filed Jul. 14, 2021.
U.S. Appl. No. 16/469,286, filed Jun. 13, 2019, US-2020/0015500 A1, Jan. 16, 2020, DeVriendt.
U.S. Appl. No. 16/636,940, filed Feb. 6, 2020, US-2020/0362373 A1, Nov. 19, 2020, Leininger.
U.S. Appl. No. 16/886,691, filed May 28, 2020, US-2020/0383353 A1, Dec. 10, 2020, Wilson.
U.S. Appl. No. 16/956,820, filed Jun. 22, 2020, US-2020/0404938 A1, Dec. 31, 2020, Heining.
U.S. Appl. No. 17/042,788, filed Sep. 28, 2020, US-2021/0024966 A1, Jan. 28, 2021, Heining.
U.S. Appl. No. 17/042,791, filed Sep. 28, 2020, US-2021/0017467 A1, Jan. 21, 2021, Adugna.
U.S. Appl. No. 17/284,463, filed Apr. 10, 2021, Erickson.
U.S. Appl. No. 17/291,608, filed May 6, 2021, Priefert.
U.S. Appl. No. 17/291,610, filed May 6, 2021, Priefert.
Saien, et al., "Effect of aqueous phase pH on liquid-liquid extraction with impinging-jets contacting technique," *Journal of Industrial and Engineering Chemistry* 16:1001-1005 (2010).
Final Office Action for copending U.S. Appl. No. 16/317,305, dated Jan. 11, 2021.
Restriction Requirement for copending U.S. Appl. No. 16/644,443, dated Dec. 21, 2021.
Response to Restriction Requirement for copending U.S. Appl. No. 16/644,443, filed Feb. 21, 2021.
Non Final Office Action for copending U.S. Appl. No. 16/644,443, dated Apr. 26, 2021.
Amendment & Response to Final Office Action for copending U.S. Appl. No. 16/317,305, filed May 7, 2021.
Amendment & Response to Non Final Office Action for copending U.S. Appl. No. 16/317,249, filed May 7, 2021.
Restriction Requirement for copending U.S. Appl. No. 16/956,453, dated May 20, 2021.
Non Final Office Action for copending U.S. Appl. No. 16/317,305, dated Jun. 4, 2021.
Non Final Office Action for copending U.S. Appl. No. 17/055,047, dated Dec. 16, 2021.
Request for Continued Examination for for copending U.S. Appl. No. 16/317,305, filed Jan. 9, 2022.
Amendment & Response to Accompany RCE for copending U.S. Appl. No. 16/317,305, filed Jan. 9, 2022.
Final Office Action for copending U.S. Appl. No. 16/317,249 dated Aug. 26, 2021.
CFSTR (Continuous Flow Stirred Tank Reactor, Chapter 8, Sec. 2, pp. 1-2, published online Dec. 2010) (Year 2010).
Non Final Office Action for copending U.S. Appl. No. 16/956,453, dated Feb. 8, 2022.
Non Final Office Action for copending U.S. Appl. No. 16/317,249, dated Mar. 24, 2022.
Notice of Allowance for copending U.S. Appl. No. 17/055,047, dated Mar. 28, 2022.
Supplemental Notice of Allowance for copending U.S. Appl. No. 17/055,047, dated Apr. 15, 2022.

\* cited by examiner

METHOD OF ISOLATING LIPIDS FROM A LIPIDS CONTAINING BIOMASS

CROSS REFERENCE TO RELATED APPLICATIONS

The present application is US national stage of international application PCT/EP2017/083712, which had an international filing date of Dec. 20, 2017, and which was published on Jul. 5, 2018. The application claims priority to European application EP 17158286.9, filed on Feb. 28, 2017 and the benefit of U.S. 62/439,354, filed on Dec. 27, 2016.

The current invention relates to a method of isolating polyunsaturated fatty acids containing lipids from a lipids containing biomass.

PUFAs (polyunsaturated fatty acids) containing lipids are of high interest in the feed, food and pharmaceutical industry. Due to overfishing there is a high need for alternative sources for PUFAs containing lipids besides fish oil. It turned out that besides certain yeast and algal strains in particular microalgal cells like those of the order Thraustochytriales are a very good source for PUFAs containing lipids.

But with respect to microbial organisms and in particular cells of the order Thraustochytriales, which produce the PUFAs containing lipids, the isolation of the oil from the cells turned out as a particular problem. The most effective way of isolating the oil was the use of organic solvents like hexane. But the use of organic solvents leads to hazardous operating conditions, requires the use of expensive explosion-proof equipment and requires the implementation of an expensive solvent recovery process to avoid pollution of the environment.

In the attempt to avoid the use of organic solvents, as an effective alternative way for isolating the oil has turned out the salting-out of the oil with high amounts of sodium chloride. But the use of high amounts of sodium chloride leads to a delipidated biomass by-product which due to the high salt content cannot be utilized as a feed ingredient, so that the process is not very sustainable. Further, the high salt concentration leads to fast corrosion of the used steel equipment.

Thus, it was the object of the current invention to provide an effective method for isolating a lipid, in particular a PUFAs containing lipid, from lipids containing cells, in particular of the order Thraustochytriales, and simultaneously avoiding not only the need of organic solvents, but further avoid the need of high amounts of salts for realizing the effective isolation of the oil from the cells.

It was a further object of the current invention to provide a method for isolating a lipid, in particular a PUFAs containing lipid, from lipids containing cells, in particular of the order Thraustochytriales, and simultaneously providing a delipidated biomass which can be utilized in a commercial way, preferably in the agricultural field.

It turned out that an effective isolation of the lipid from the biomass can be realized, if the biomass, in particular after lysing, is incubated with a specific amount of base equivalents, preferably at a low alkaline pH and at a temperature of not more than 100° C. By keeping the temperature well below 100° C., it was possible to prohibit at least essentially saponification of the fatty acid esters.

It was very surprising according to the invention to find out that when a specific, well-defined amount of base equivalents is added to the amount of biomass as contained in the suspension, which must neither be too low nor too high, that then the pH and temperature and even the time of exposure do not seem to play an important role for realizing an efficient demulsification. That means that the separation of the oil from the residual biomass could be carried out under very mild conditions for the contained PUFAs as well as under very economic circumstances, as low temperature and low exposure time means low energy input and in addition a saving of time.

Thus, a first subject of the current invention is a method of isolating a polyunsaturated fatty acids (PUFAs) containing lipid from a biomass, comprising the following steps:
  a) Providing a suspension of a biomass comprising cells which contain a PUFAs containing lipid;
  b) Optionally lysing the cells of the biomass;
  c) Concentrating the suspension to a total dry matter (TDM) content of 20 to 60 wt.-%, preferably 25 to 60 wt.-%, more preferably 30 to 55 wt.-%, if the suspension has a lower TDM content;
  d) Adjusting in the suspension a temperature of 20° C. to 100° C., preferably 25, 30, 40, 50 or 60° C. to 100° C., more preferably 65° C. to 95° C., in particular 70 to 90° C.;
  e) Keeping the temperature in the ranges as depicted in (d) for at least 1 hour, preferably for at least 2, 3, 4, 5, 6, 7 or 8 hours, more preferably for 1 to 36 hours, in particular for 2, 3, 4, 5, 6, 7 or 8 hours to 36 hours, more preferably 10 to 24 hours, while adding in total 7.5 to 25 moles, preferably 8.5 to 22 moles, in particular 10 to 20, more preferably 11 to 18, above all 12 to 17, in particular 12 to 15, moles, of base equivalent to 10 kg of total dry matter as contained in the suspension of the optionally lysed biomass.

It was very surprising in this context that the demulsification could be carried out efficiently even at a temperature below 80° C., and in particular at a temperature below 60° C.

Thus, a particular subject of the current invention is a method of isolating a polyunsaturated fatty acids (PUFAs) containing lipid from a biomass, comprising the following steps:
  a) Providing a suspension of a biomass comprising cells which contain a PUFAs containing lipid;
  b) Optionally lysing the cells of the biomass;
  c) Concentrating the suspension to a total dry matter (TDM) content of 20 to 60 wt.-%, preferably 25 to 60 wt.-%, more preferably 30 to 55 wt.-%, if the suspension has a lower TDM content;
  d) Adjusting in the suspension a temperature of 20° C. to below 80° C., preferably a temperature of 25° C. to below 60° C., more preferably 25° C. to 58° C., in particular 30 to 55° C., above all a temperature of 30° C. to 50° C.;
  e) Keeping the temperature in the ranges as depicted in (d) for at least 1 hour, preferably for at least 2, 3, 4, 5, 6, 7 or 8 hours, more preferably for 1 to 36 hours, in particular for 2, 3, 4, 5, 6, 7 or 8 hours to 36 hours, more preferably 10 to 24 hours, while adding in total 7.5 to 25 mole, preferably 8.5 to 22 mole, in particular 10 to 20, more preferably 11 to 18, above all 12 to 17, in particular 12 to 15, moles of base equivalent to 10 kg of total dry matter as contained in the suspension of the optionally lysed biomass.

It was also very surprising in this context that the demulsification could be carried out efficiently at a pH below 9.0.

Thus, a further particular subject of the current invention is a method of isolating a polyunsaturated fatty acids (PUFAs) containing lipid from a biomass, comprising the following steps:

a) Providing a suspension of a biomass comprising cells which contain a PUFAs containing lipid;
b) Optionally lysing the cells of the biomass;
c) Concentrating the suspension to a total dry matter (TDM) content of 20 to 60 wt.-%, preferably 25 to 60 wt.-%, more preferably 30 to 55 wt.-%, if the suspension has a lower TDM content;
d) Adjusting in the suspension a temperature of 20° C. to 100° C., preferably 25, 30, 40, 50 or 60° C. to 100° C., more preferably 65° C. to 95° C., in particular 70 to 90° C.;
e) Keeping the temperature in the ranges as depicted in (d) for at least 1 hour, preferably for at least 2, 3, 4, 5, 6, 7 or 8 hours, more preferably for 1 to 36 hours, in particular for 2, 3, 4, 5, 6, 7 or 8 hours to 36 hours, more preferably 10 to 24 hours, while adding in total 7.5 to 25 mole, preferably 8.5 to 22 mole, in particular 10 to 20, more preferably 11 to 18, above all 12 to 17, in particular 12 to 15, moles of base equivalent to 10 kg of total dry matter as contained in the suspension of the optionally lysed biomass, while the pH of the composition is always kept below 9.0, preferably always kept below 8.5, in particular kept in the range of 8.0 to 8.9, in particular in the range of 8.0 to 8.4.

It was also surprising in this context that the demulsification can be carried out efficiently at an exposure time of below 10 hours.

Thus, a further subject of the current invention is a method of isolating a polyunsaturated fatty acids (PUFAs) containing lipid from a biomass, comprising the following steps:
a) Providing a suspension of a biomass comprising cells which contain a PUFAs containing lipid;
b) Optionally lysing the cells of the biomass;
c) Concentrating the suspension to a total dry matter (TDM) content of 20 to 60 wt.-%, preferably 25 to 60 wt.-%, more preferably 30 to 55 wt.-%, if the suspension has a lower TDM content;
d) Heating the suspension to a temperature of 20° C. to 100° C., preferably 25, 30, 40, 50 or 60° C. to 100° C., more preferably 65° C. to 95° C., in particular 70 to 90° C.;
e) Keeping the temperature in the ranges as depicted in (c) for less than 10 hours, in particular for 1 to less than 10 hours, preferably not more than 8 hours, in particular 1 or 2 to 8 hours, more preferably for not more than 6 hours, in particular 1, 2 or 3 to 6 hours, while adding in total 7.5 to 25 mole, preferably 8.5 to 22 mole, in particular 10 to 20, more preferably 11 to 18, above all 12 to 17, in particular 12 to 15, moles of base equivalent to 10 kg of total dry matter as contained in the suspension of the optionally lysed biomass.

It was also surprising according to the invention that the demulsification could be carried out without prior lysing of the cells of the biomass.

Thus, a further subject of the current invention is a method of isolating a polyunsaturated fatty acids (PUFAs) containing lipid from a biomass, comprising the following steps:
a) Providing a suspension of a biomass comprising cells which contain a PUFAs containing lipid;
c) Concentrating the suspension to a total dry matter (TDM) content of 20 to 60 wt.-%, preferably 25 to 60 wt.-%, more preferably 30 to 55 wt.-%, if the suspension has a lower TDM content;
d) Heating the suspension to a temperature of 20° C. to 100° C., preferably 25, 30, 40, 50 or 60° C. to 100° C., more preferably 65° C. to 95° C., in particular 70 to 90° C.;
e) Keeping the temperature in the range as depicted in (c) for at least 1 hour, preferably for at least 2, 3, 4, 5, 6, 7 or 8 hours, more preferably for 1 to 36 hours, in particular for 2, 3, 4, 5, 6, 7 or 8 hours to 36 hours, more preferably 10 to 24 hours, while adding in total 7.5 to 25 moles, preferably 8.5 to 22 moles, in particular 10 to 20, more preferably 11 to 18, above all 12 to 17, in particular 12 to 15, moles, of base equivalent to 10 kg of total dry matter as contained in the suspension,
characterized in that steps (d) and (e) are carried out without prior lysing of the cells of the biomass.

If not indicated otherwise, then the pH is according to the invention preferably kept in step (e) below 11.5, more preferably below 11, more preferably below 10.5, in particular in the range of 8 to 11.5, more preferably in the range of 9 to 11, in particular in the range of 10 to 11. This is realized by adding the base in step (e) not at once, but either continuously or step by step, so that exceeding the indicated pH values can be avoided.

In the methods according to the invention, the steps (d) and (e) lead to the breaking of the emulsion as contained in the suspension into an oil containing light phase and a water, cell debris and salts containing heavy phase. This breaking of the emulsion is also called "demulsification" in the context of this application.

Preferably, in the steps (b) to (e) of the method the suspension is continuously mixed by using a stirrer and/or an agitator. In the method steps (d) and/or (e) preferably low shear agitation and/or axial-flow agitation is applied, in particular as disclosed in WO 2015/095694. Impellers suitable for agitating prior and during steps (d) and/or (e) include in particular straight blade impellers, Rushton blade impellers, axial flow impellers, radial flow impellers, concave blade disc impellers, high-efficiency impellers, propellers, paddles, turbines and combinations thereof.

The term "base equivalent" takes account of the fact that not only monovalent, but also bi- or multivalent bases do exist and can be used according to the invention. In case that a bivalent base is used instead or in addition to a monovalent base, then only the half molar amount of this bivalent base has to be used to realize the same amount of base equivalents in comparison to the amount of monovalent base which would have to be used; in case a trivalent base is used, then only a third of the molar amount of monovalent base has to be used; etc. In case that a monovalent base, like sodium hydroxide, is used, the amount of base equivalents is identical to the amount of base.

The weight amount of base can easily be calculated basing on the molar amount by making use of the molar weight of the base. For example, in case of the very preferred base sodium hydroxide the molar weight equals to 40 g/mol. That means that one mole of sodium hydroxide corresponds to 40 g of sodium hydroxide.

Preferred bases as used according to the invention are selected from hydroxides, in particular sodium hydroxide, lithium hydroxide, potassium hydroxide, and/or calcium hydroxide, carbonates, in particular sodium carbonate, potassium carbonate, and/or magnesium carbonate, and/or bicarbonates, in particular lithium bicarbonate, sodium bicarbonate, and/or potassium bicarbonate. In a very preferred embodiment of the invention, the base used according to the invention is only or almost only sodium hydroxide.—Due to easiness of handling, the bases are preferably used in liquid form, in particular as concentrated solutions, wherein the concentration of base in the solution is preferably in the range of 10 to 60 wt.-%, in particular in the range of 20 to 50 wt.-%.

According to the invention after providing the suspension according to step (a) preferably a lysing step is carried out. The lysing step can be omitted, if—for example due to the fermentation conditions as applied—the cells or a big part thereof is already lysed or easily breakable in one of the following steps of the procedure without any explicit lysing step.

Lysing of the cells of the biomass according to step (b) can be carried out by methods as known to those skilled in the art, in particular enzymatically, mechanically, physically, or chemically, or by applying combinations thereof.

Depending on the time of exposure and/or the degree of force applied, a composition comprising only lysed cells or a composition comprising a mixture of cell debris and intact cells may be obtained. The term "lysed lipids containing biomass" insofar relates to a suspension which contains water, cell debris and oil as set free by the cells of the biomass, but beyond that may also comprise further components, in particular salts, intact cells, further contents of the lysed cells as well as components of a fermentation medium, in particular nutrients. In a preferred embodiment of the invention, only small amounts of intact cells, in particular less than 20%, preferably less than 10%, more preferably less than 5% (relating to the total number of intact cells as present before lysing the cells of the biomass) are present in the lysed biomass after the step of lysing the cells.

Lysing of the cells may be realized for example by utilizing a French cell press, sonicator, homogenizer, microfluidizer, ball mill, rod mill, pebble mill, bead mill, high pressure grinding roll, vertical shaft impactor, industrial blender, high shear mixer, paddle mixer, and/or polytron homogenizer.

In a preferred embodiment of the invention, lysing of the cells comprises an enzymatic treatment of the cells by applying a cell-wall degrading enzyme.

According to the invention, the cell-wall degrading enzyme is preferably selected from proteases, cellulases (e.g., Cellustar CL (Dyadic), Fibrezyme G2000 (Dyadic), Celluclast (Novozymes), Fungamyl (Novozymes), Viscozyme L (Novozymes)), hemicellulases, chitinases, pectinases (e.g., Pectinex (Novozymes)), sucrases, maltases, lactases, alpha-glucosidases, beta-glucosidases, amylases (e.g., Alphastar Plus (Dyadic); Termamyl (Novozymes)), lysozymes, neuraminidases, galactosidases, alpha-mannosidases, glucuronidases, hyaluronidases, pullulanases, glucocerebrosidases, galactosylceramidases, acetylgalactosaminidases, fucosidases, hexosaminidases, iduronidases, maltases-glucoamylases, xylanases (e.g., Xylanase Plus (Dyadic), Pentopan (Novozymes)), beta-glucanases (e.g., Vinoflow Max (Novozymes), Brewzyme LP (Dyadic)), mannanases, and combinations thereof. The protease may be selected from serine proteases, threonine proteases, cysteine proteases, aspartate proteases, metalloproteases, glutamic acid proteases, alcalases (subtilisins), and combinations thereof. The chitinase may be a chitotriosidase. The pectinase may be selected from pectolyases, pectozymes, polygalacturonases, and combinations thereof.

The adequate pH for utilizing the enzyme depends on the pH optimum of the enzyme.

In a preferred embodiment of the invention, an enzyme with a pH optimum of between 7.0 and 8.0, in particular of about 7.5, is used, so that the pH applied in this step is from 7.0 to 8.0, preferably from 7.3 to 7.7. A preferred enzyme which can be used in this pH range is an alcalase.

The enzyme is preferably added as a concentrated enzyme solution, preferably in an amount of 0.01 to 1.5 wt.-%, more preferably in an amount of 0.03 to 1.0 wt.-%, above all in an amount of 0.05 to 0.5 wt.-%, relating to the amount of concentrated enzyme solution as added in relation to the total amount of the suspension after addition of the concentrated enzyme solution.

In a very preferred embodiment of the invention, lysing of the cells is carried out as follows:
 i) Heating the suspension of (a) to a temperature of between 50° C. and 70° C., preferably to a temperature of between 55° C. and 65° C., and adding a cell wall-degrading enzyme to the suspension, in particular fermentation broth, and adjusting an adequate pH value, if necessary, at which the enzyme is properly working;
 ii) Keeping the temperature and pH in the ranges as depicted in (ii) for at least one hour, preferably for at least two hours, more preferably for two to four hours.

In step (i), the enzyme can be added before or after heating up the suspension and/or before or after adjusting the pH. In the same way heating up of the suspension can be carried out before or after adjusting the pH. —But in a preferred embodiment, the enzyme is added after heating up of the suspension and after adjusting the pH, if adjusting of the pH is necessary, at all. —In a very preferred embodiment all measures are carried out more or less simultaneously.

Preferably, in the steps (i) and (ii) the suspension is continuously mixed by using a stirrer and/or an agitator.

According to the invention, the demulsification is carried out with a suspension having a dry matter content of 20 to 60 wt.-%, preferably 25 to 60 wt. %, in particular 30 to 55 wt.-% or 30 to 45 wt.-%. This can be realized by either providing a suspension with an appropriately high biomass in step (a) or by concentrating the suspension, in particular after lysing the cells of the biomass. Thus, in a preferred embodiment of the invention, after optional lysing of the cells of the biomass and before the demulsification step, the suspension is concentrated to a total dry matter content of 20 to 60 wt.-%, more preferably 25 to 60 wt.-%, in particular 30 to 55 wt.-%, above all 30 to 50 wt.-% or 30 to 45 wt.-%.

Concentration of the suspension is preferably carried out by evaporation of water at a temperature not higher than 100° C., preferably 70° C. to 100° C., more preferably 80° C. to 90° C., until a total dry matter content of 20 to 60 wt.-% more preferably 25 to 60 wt.-%, in particular 30 to 55 wt.-% or 30 to 45 wt.-%, is reached.

Concentration of the suspension is preferably carried out in a forced circulation evaporator (for example available from GEA, Germany) to allow fast removal of the water. Alternatively or in addition, concentration might be carried out by falling film evaporation, thin film evaporation and/or rotary evaporation.

In general, adjusting the pH value can be carried out according to the invention by using either bases or acids as known to those skilled in the art. Decreasing of the pH can be carried out in particular by using organic or inorganic acids like sulfuric acid, nitric acid, phosphoric acid, boric acid, hydrochloric acid, hydrobromic acid, perchloric acid, hypochlorous acid, chlorous acid, fluorosulfuric acid, hexafluorophosphoric acid, acetic acid, citric acid, formic acid, or combinations thereof. As a high content of chloride is desirably avoided, in a preferred embodiment of the invention no or only small amounts of hydrochloric acid are used in the process of the current invention. According to the invention, sulfuric acid is the preferred substance for decreasing the pH value. —Increasing of the pH can be carried out in particular by using organic or inorganic bases like hydroxides, in particular sodium hydroxide, lithium hydroxide, potassium hydroxide, and/or calcium hydroxide, carbonates, in particular sodium carbonate, potassium carbonate, or magnesium carbonate, and/or bicarbonates, in particular lithium bicarbonate, sodium bicarbonate, and/or potassium bicarbonate. —Due to easiness of handling, the acids and bases are preferably used in liquid form, in particular as concentrated solutions, wherein the concentration of acid or base in the solution is preferably in the range of 10 to 55 wt.-%, in particular in the range of 20 to 50 wt.-%. In particular sulfuric acid is preferably used also in concentrated form.

The method according to the invention preferably comprises as a further step the harvesting of the PUFAs containing lipid from the demulsified composition as obtained in step (e).

The harvesting of the PUFAs containing lipid preferably comprises neutralization of the demulsified suspension and subsequent separation of the thus obtained oil containing light phase from the water, salts, cell debris and residual oil containing heavy phase.

Neutralization of the demulsified composition is preferably realized by adding an acid, preferably sulfuric acid, to adjust a pH value of 5.5 to 8.5, in particular 6.5 to 8.5, preferably 6.5 to 7.5 or 7.0 to 8.0. Before starting separation of the light phase from the heavy phase the neutralized composition may be stirred at this neutralized pH from several minutes up to several hours. —Neutralization of the demulsified composition is only necessary in this embodiment for sure, if the demulsified composition as obtained according to step (e) of the methods of the invention has a pH value outside of this range.

Separation of the oil containing light phase from the water, salts and cell debris containing heavy phase is preferably realized by mechanical means and preferably at a temperature of 60-90° C., more preferably 70-80° C., and preferably at a pH value of 6-9, more preferably 7-8.5. "Mechanical means" refers in particular to filtration and centrifugation methods as known to those skilled in the art.

After separation of the oil containing light phase, the PUFAs containing oil thus obtained can further be worked up by applying methods as known to those skilled in the art, in particular refining, bleaching, deodorizing and/or winterizing.

A particular advantage of the method of the current invention is that it can be carried out without the use of any organic solvent, in particular without the use of any polar or non-polar organic solvent. Thus, in a preferred embodiment of the invention, no or only little amounts of organic solvents, in particular of polar or non-polar organic solvents, are used for isolating the PUFAs containing oil from the biomass. Typical organic solvents are hexane and ethanol.

In a preferred embodiment of the invention less than 2 wt.-% non-polar organic solvents are used, more preferably less than 1, 0.5 or 0.1 wt.-%. In a particularly preferred embodiment of the invention no non-polar organic solvent is used, at all. In a very preferred embodiment of the invention less than 2 wt.-% organic solvents are used, in general, particularly preferred less than 1, 0.5 or 0.1 wt.-%. In a particularly very preferred embodiment of the invention no organic solvents are used, at all.

A further advantage of the method of the current invention is that a very efficient separation of the oil from the remaining biomass can be realized without the addition of sodium chloride, which is normally used for salting out the oil from the biomass. Preferably the method can be carried out without the addition of chloride salts, at all, above all without the addition of any salts for salting out the oil. But small amounts of chloride salts, in particular sodium chloride, might be present in the suspension due to the fermentation medium as used for growing of the biomass.

Thus, in a preferred embodiment of the current invention, no or only little amounts of sodium chloride are used for improving the oil isolation. In a preferred embodiment of the invention less than 1 wt.-% of sodium chloride, are used, more preferably less than 0.5 or 0.2 wt.-% of sodium chloride are used for isolating the oil from the biomass, above all less than 0.1 or 0.05 wt.-%, wherein the wt.-% relate to the total weight of the composition after addition of the sodium chloride.

In a particularly preferred embodiment of the invention no or only little amounts of chloride salts are used for improving the oil isolation, at all. In this embodiment preferably less than 1 wt.-% of chloride salts, more preferably less than 0.5 or 0.2 wt.-% of chloride salts are used for isolating the oil from the biomass, above all less than 0.1 or 0.05 wt.-%, wherein the wt.-% relate to the total weight of the composition after addition of the chloride salts.

In a very preferred embodiment of the invention no or only little amounts of salts are used for improving the oil isolation, in general. In this embodiment preferably less than 1 wt.-% of salts, more preferably less than 0.5 or 0.2 wt.-% of salts are used for isolating the oil from the biomass, above all less than 0.1 or 0.05 wt.-%, wherein the wt.-% relate to the total weight of the composition after addition of the salts.

The methods of the current invention allow a very efficient separation of the oil contained in the biomass from the cell-debris and other substances as contained in the suspension, in particular fermentation broth. By using the methods of the current invention preferably more than 80 wt.-%, in particular more than 90 wt.-% of the oil contained in the biomass can be separated from the biomass and isolated by applying very economic and sustainable conditions.

"Chloride" according to the invention refers to the amount of detectable chlorine. The amount of chlorine as present can be determined for example by elemental analysis according to DIN EN ISO 11885. The chlorine is present in the form of salts which are called "chlorides". The content of chloride as mentioned according to the invention—also called "chloride ions"—only refers to the amount of detectable chlorine, not to the amount of the complete chloride salt, which comprises besides the chloride ion also a cationic counterion.

The total dry matter content (TDM) is preferably determined by gravimetric analysis. For doing that, a sample of the homogeneous suspension with a specific volume is weighed before and after freeze-drying. The remaining weight of the dried sample corresponds to the total dry matter as contained in that specific volume of the suspension.

The yield of liberated oil is preferably determined by fatty acid methyl ester analysis (FAME). For doing that the lipids in the sample are first saponified with KOH. After that, the free fatty acids are methylated with MeOH. The methylated fatty acids can then be determined and quantified by gas chromatography by using an internal standard.

In a particularly preferred embodiment of the current invention the water, salts, residual oil and cell debris containing aqueous phase, which is obtained as by-product in the oil harvesting step as described before, is converted into a dried biomass by drying the biomass to a total dry matter content of more than 90 wt.-%.

Conversion of the water, salts, remaining oil and cell debris containing heavy phase, which is obtained as by-product in the oil harvesting step, into a dried biomass by drying the biomass to a total dry matter content of more than 90 wt.-%, can be carried out in different ways.

In a very preferred way, the transformation is carried out by concentration of the heavy phase to a dry matter content of 30-50 wt.-%, preferably 35-45 wt.-%, and subsequent spray granulation of the biomass by means of fluidized bed granulation. By doing that, in a very efficient way, a biomass with advantageous features can be obtained. Spray granulation by means of fluidized bed granulation is disclosed in more detail in EP13176661.0.

Concentration of the heavy phase to a dry matter content of 30-50 wt.-% is preferably carried out by solvent evaporation, in particular vacuum evaporation, and/or by using a rotary evaporator, a thin-film evaporator or a falling-film evaporator. A useful alternative to solvent evaporation is reverse osmosis.

As alternative to the spray-granulation other drying methods, in particular other convective drying methods, like tunnel drying or spray drying, in particular nozzle spray drying, or contact drying methods, like drum drying, or radiation drying methods, like infrared drying, of the concentrated heavy phase would be applicable alternatives, wherein by using those methods normally particles with a smaller or bigger diameter are obtained.

According to the invention, during the drying process, an anti-caking agent, in particular silica, preferably a hydrophobic or hydrophilic silica, may optionally be added to the biomass to prevent caking. For this purpose, the suspension, in particular fermentation broth, comprising biomass as well as the silica are preferably sprayed into the particular drying zone. Alternatively or additionally, the biomass may be mixed with the anti-caking agent after the drying process. With respect to the use of silica as anti-caking agent reference is made in particular to the patent application EP13187631.0.

Conversion of a fine-grained powder into a coarse-grained dust-free product can be realized by granulating processes. Conventional organic or inorganic auxiliaries or supports such as starch, gelatin, cellulose derivatives or similar substances, which are typically used in food processing or feed processing as binding agents, gelling agents or thickeners, may optionally be used in this subsequent granulation process. Further auxiliaries that are preferably used according to the invention are disclosed in WO 2016/050560, with carboxymethylcellulose being a particularly preferred binding agent. After drying and optionally granulating and/or sieving of the biomass, the dried biomass is preferably stored or packed.

The particulate biomass of the invention as well as the aqueous suspensions of the invention can be used in different ways. For example, they can be used in order to produce a foodstuff or feedstuff. Alternatively they may be used directly as foodstuff or feedstuff.

A further subject matter of the present invention is therefore likewise a method for producing a feedstuff or foodstuff, in which a particulate biomass and/or an aqueous suspension according to the invention is used, and is preferably mixed with further feedstuff or foodstuff ingredients.

The PUFAs containing cells of the biomass are preferably microbial cells or plant cells. Preferably, the cells are capable of producing the PUFAs due to a polyketide synthase system. The polyketide synthase system may be an endogenous one or, due to genetic engineering, an exogenous one.

The plant cells may in particular be selected from cells of the families Brassicaceae, Elaeagnaceae and Fabaceae. The cells of the family Brassicaceae may be selected from the genus *Brassica*, in particular from oilseed rape, turnip rape and Indian mustard; the cells of the family Elaeagnaceae may be selected from the genus *Elaeagnus*, in particular from the species *Oleae europaea*; the cells of the family Fabaceae may be selected from the genus *Glycine*, in particular from the species *Glycine max*.

The microbial organisms which contain a PUFAs containing lipid are described extensively in the prior art. The cells used may, in this context, in particular be cells which already naturally produce PUFAs (polyunsaturated fatty acids); however, they may also be cells which, as the result of suitable genetic engineering methods or due to random mutagenesis, show an improved production of PUFAs or have been made capable of producing PUFAs, at all. The production of the PUFAs may be auxotrophic, mixotrophic or heterotrophic.

The biomass preferably comprises cells which produce PUFAs heterotrophically. The cells according to the invention are preferably selected from algae, fungi, particularly yeasts, bacteria, or protists. The cells are more preferably microbial algae or fungi.

Suitable cells of oil-producing yeasts are, in particular, strains of *Yarrowia*, *Candida*, *Rhodotorula*, *Rhodosporidium*, *Cryptococcus*, *Trichosporon* and *Lipomyces*.

Suitable cells of oil-producing microalgae and algae-like microorganisms are, in particular, microorganisms selected from the phylum Stramenopiles (also called Heterokonta). The microorganisms of the phylum Stramenopiles may in particular be selected from the following groups of microorganisms: Hamatores, Proteromonads, Opalines, Developayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinales, Pedinellales, Dictyochales), Chrysomeridales, Sarcinochrysidales, Hydrurales, Hibberdiales, and Chromulinales. Other preferred groups of microalgae include the members of the green algae and dinoflagellates, including members of the genus *Crypthecodiurn*.

The biomass according to the invention preferably comprises cells, and preferably consists essentially of such cells, of the taxon Labyrinthulomycetes (Labyrinthulea, net slime fungi, slime nets), in particular those from the family of Thraustochytriaceae. The family of the Thraustochytriaceae (Thraustochytrids) includes the genera *Althomia*, *Aplanochytrium*, *Aurantiochytrium*, *Botryochytrium*, *Elnia*, *Japonochytrium*, *Oblongichytrium*, *Parietichytrium*, *Schizochytrium*, *Sicyoidochytrium*, *Thraustochytrium*, and *Ulkenia*. The biomass particularly preferably comprises cells from the genera *Aurantiochytrium*, *Oblongichytrium*, *Schizochytrium*, or *Thraustochytrium*, above all from the genus *Schizochytrium*.

In accordance with the invention, the polyunsaturated fatty acid (PUFA) is preferably a highly-unsaturated fatty acid (HUFA).

The cells present in the biomass are preferably distinguished by the fact that they contain at least 20% by weight, preferably at least 30% by weight, in particular at least 35% by weight, of PUFAs, in each case based on cell dry matter.

According to the current invention, the term "lipid" includes phospholipids; free fatty acids; esters of fatty acids; triacylglycerols; sterols and sterol esters; carotenoids; xanthophylls (e. g. oxycarotenoids); hydrocarbons; isoprenoid-derived compounds and other lipids known to one of ordinary skill in the art. —The terms "lipid" and "oil" are used interchangeably according to the invention.

In a preferred embodiment, the majority of the lipids in this case is present in the form of triglycerides, with preferably at least 50% by weight, in particular at least 75% by weight and, in an especially preferred embodiment, at least 90% by weight of the lipids present in the cell being present in the form of triglycerides.

According to the invention, polyunsaturated fatty acids (PUFAs) are understood to mean fatty acids having at least two, particularly at least three, C—C double bonds. According to the invention, highly-unsaturated fatty acids (HUFAs) are preferred among the PUFAs. According to the invention, HUFAs are understood to mean fatty acids having at least four C—C double bonds.

The PUFAs may be present in the cell in free form or in bound form. Examples of the presence in bound form are phospholipids and esters of the PUFAs, in particular monoacyl-, diacyl- and triacylglycerides. In a preferred embodiment, the majority of the PUFAs is present in the form of triglycerides, with preferably at least 50% by weight, in particular at least 75% by weight and, in an especially preferred embodiment, at least 90% by weight of the PUFAs present in the cell being present in the form of triglycerides.

Preferred PUFAs are omega-3 fatty acids and omega-6 fatty acids, with omega-3 fatty acids being especially preferred. Preferred omega-3 fatty acids here are the eicosapentaenoic acid (EPA, 20:5ω-3), particularly the (5Z,8Z,11Z,14Z,17Z)-eicosa-5,8,11,14,17-pentaenoic acid, and the docosahexaenoic acid (DHA, 22:6ω-3), particularly the (4Z,7Z,10Z,13Z,16Z,19Z)-docosa-4,7,10,13,16,19-hexaenoic acid.

In a very preferred embodiment of the current invention, cells, in particular a *Schizochytrium* strain, is employed which produces a significant amount of EPA and DHA, simultaneously, wherein DHA is preferably produced in an amount of at least 20 wt.-%, preferably in an amount of at least 30 wt.-%, in particular in an amount of 30 to 50 wt.-%, and EPA is produced in an amount of at least 5 wt.-%, preferably in an amount of at least 10 wt.-%, in particular in an amount of 10 to 20 wt.-% (in relation to the total amount of lipid as contained in the cells, respectively). DHA and EPA producing *Schizochytrium* strains can be obtained by consecutive mutagenesis followed by suitable selection of mutant strains which demonstrate superior EPA and DHA production and a specific EPA:DHA ratio. Any chemical or nonchemical (e.g. ultraviolet (UV) radiation) agent capable of inducing genetic change to the yeast cell can be used as the mutagen. These agents can be used alone or in combination with one another, and the chemical agents can be used neat or with a solvent.

Preferred species of microorganisms of the genus *Schizochytrium*, which produce EPA and DHA simultaneously in significant amounts, as mentioned before, are deposited under ATCC Accession No. PTA-10208, PTA-10209, PTA-10210, or PTA-10211, PTA-10212, PTA-10213, PTA-10214, PTA-10215.

The suspension of biomass according to the present invention has preferably a biomass density of at least 80 or 100 g/l, in particular a biomass density of 80 to 250 g/l, in particular 80 to 200 g/l, more preferably a biomass density of at least 120 or 140 g/l, in particular at least 160 or 180 g/l (calculated as dry-matter content) and is preferably a fermentation broth. Thus, the suspension may be obtained by culturing and growing suitable cells in a fermentation medium under conditions whereby the PUFAs are produced by the microorganism.

Methods for producing the biomass, in particular a biomass which comprises cells containing lipids, in particular PUFAs, particularly of the order Thraustochytriales, are described in detail in the prior art (see e.g. WO91/07498, WO94/08467, WO97/37032, WO97/36996, WO01/54510). As a rule, the production takes place by cells being cultured in a fermenter in the presence of a carbon source and of a nitrogen source, along with a number of additional substances like minerals that allow growth of the microorganisms and production of the PUFAs. In this context, biomass densities of more than 100 grams per litre and production rates of more than 0.5 gram of lipid per litre per hour may be attained. The process is preferably carried out in what is known as a fed-batch process, i.e. the carbon and nitrogen sources are fed in incrementally during the fermentation. When the desired biomass has been obtained, lipid production may be induced by various measures, for example by limiting the nitrogen source, the carbon source or the oxygen content or combinations of these.

In a preferred embodiment of the current invention, the cells are grown until they reach a biomass density of at least 80 or 100 g/l, more preferably at least 120 or 140 g/l, in particular at least 160 or 180 g/l (calculated as total dry matter content). Such processes are for example disclosed in U.S. Pat. No. 7,732,170.

Preferably, the cells are fermented in a medium with low salinity, in particular so as to avoid corrosion. This can be achieved by using chlorine-free sodium salts as the sodium source instead of sodium chloride, such as, for example, sodium sulphate, sodium carbonate, sodium hydrogen carbonate or soda ash. Preferably, chloride is used in the fermentation in amounts of less than 3 g/l, in particular less than 500 mg/l, especially preferably less than 100 mg/l.

Suitable carbon sources are both alcoholic and non-alcoholic carbon sources. Examples of alcoholic carbon sources are methanol, ethanol and isopropanol. Examples of non-alcoholic carbon sources are fructose, glucose, sucrose, molasses, starch and corn syrup.

Suitable nitrogen sources are both inorganic and organic nitrogen sources. Examples of inorganic nitrogen sources are nitrates and ammonium salts, in particular ammonium sulphate and ammonium hydroxide. Examples of organic nitrogen sources are amino acids, in particular glutamate, and urea.

In addition, inorganic or organic phosphorus compounds and/or known growth-stimulating substances such as, for example, yeast extract or corn steep liquor, may also be added so as to have a positive effect on the fermentation.

The cells are preferably fermented at a pH of 3 to 11, in particular 4 to 10, and preferably at a temperature of at least 20° C., in particular 20 to 40° C., especially preferably at least 30° C. A typical fermentation process takes up to approximately 100 hours.

After the fermentation has ended, the cells may be pasteurized in order to kill the cells and to deactivate enzymes which might promote lipid degradation. The pasteurization is preferably effected by heating the biomass to a temperature of 50 to 121° C., preferably 50 to 70° C., for a period of 5 to 150 minutes, in particular 20 to 100 minutes.

Likewise, after the fermentation is ended, antioxidants may be added in order to protect the PUFAs present in the biomass from oxidative degradation. Preferred antioxidants in this context are BHT, BHA, TBHA, ethoxyquin, beta-carotene, vitamin E, in particular tocopherol, and vitamin C. The antioxidant, if used, is preferably added in an amount of 0.001 to 0.1 wt.-%, preferably in an amount of 0.002 to 0.05 wt.-%, relating to the total amount of the fermentation broth after addition of the antioxidant.

WORKING EXAMPLES

Example 1: Preparation of the Suspension for Use in the Demulsification Tests

An unwashed cell broth containing microbial cells (*Schizochytrium* sp.) at a biomass density of over 100 g/l was heated to 60° C. in an agitated vessel. After heating up the suspension, the pH was adjusted to 7.5 by using caustic soda (50 wt.-% NaOH solution), before an alcalase (Alcalase® 2.4 FG (Novozymes)) was added in liquid form in an amount of 0.5 wt.-% (by weight broth). Stirring was continued for 3 hours at 60° C. After that, the lysed cell mixture was transferred into a forced circulation evaporator (obtained from GEA, Germany) and heated to a temperature of 85° C. The mixture was concentrated in the forced circulation evaporator, until a total dry matter content of about 30 wt.-% was reached.

Example 2: Influence of the Amount of Added Base Equivalents on the Liberation of the Oil To test the significance of the amount of added base equivalents on the efficiency of the oil liberation from the biomass, the effect of addition of different amounts of caustic soda to the biomass with respect to the liberation of oil was tested. The ratio of base equivalents added to total dry matter is depicted in table 1 as well as the amount of oil as set free by the addition of the caustic soda. All experiments were carried out with one liter of enzymatically treated and subsequently concentrated fermentation broth using a stirring vessel BIOSTAT® B-DCU-Quad 2L (Sartorius, Germany). The total dry matter of the samples was 30 wt.-%. Demulsification was carried out for 24 hours at a temperature of 80° C. The suspension was stirred with 300 rpm. Caustic soda was added at the beginning as one shot. After 24 hours, the demulsified compositions were neutralized to pH 7.5. After neutralization, a 50 g sample of the homogenized suspension was taken and separation of the cell debris was carried out by centrifugation at 13500 g. Subsequently the amount of EPA and DHA in the supernatant was determined.

TABLE 1

Influence of the amount of added NaOH on the amount of liberated oil

| | Added amount of NaOH [mol/10 kg TDM] | | | |
|---|---|---|---|---|
| | 10 | 12.5 | 15 | 22.5 |
| Added amount of NaOH [wt.-%/TDM] | 4 | 5 | 6 | 9 |
| Yield [wt.-%] | 90.8 | 91.9 | 93.4 | 87.7 |

The results show that even with quite low amounts of added base equivalents already very good yields of liberated oil can be realized without addition of organic solvents or salts like sodium chloride. Further it becomes clear that there is a ratio of added base equivalent to total dry matter, where a maximized yield can be realized. Further increasing the amount of base equivalents beyond that ratio do not increase the yield, but leads to even worse results in comparison to smaller amounts of added base equivalents. Best results were obtained with an amount of 12.5 and 15 moles NaOH per 10 kg of TDM.

Example 3: Influence of the Amount of Added Base Equivalents on the Liberation of the Oil To further test the significance of the amount of added base equivalents on the efficiency of the oil liberation from the biomass, the effect of addition of different amounts of caustic soda to the biomass with respect to the liberation of oil was tested. The ratio of base equivalents added to total dry matter is depicted in table 2 as well as the amount of oil as set free by the addition of the caustic soda. All experiments were carried out with one liter of enzymatically treated and subsequently concentrated fermentation broth using a stirring vessel BIOSTAT® B-DCU-Quad 2L (Sartorius, Germany). The total dry matter of the samples was 30.5 wt.-%. Demulsification was carried out for 24 hours at a temperature of 80° C. The suspension was stirred with 300 rpm. Caustic soda was added stepwise in three shots to keep the pH low. After 24 hours the demulsified compositions were neutralized to pH 7.5. After neutralization, a 50 g sample of the homogenized suspension was taken and separation of the cell debris was carried out by centrifugation at 13500 g. Subsequently the amount of EPA and DHA in the supernatant was determined.

TABLE 2

Influence of the amount of added NaOH on the amount of liberated oil

| | Added amount of NaOH [mol/10 kg TDM] | | | |
|---|---|---|---|---|
| | 12.5 | 17.5 | 20 | 22.5 |
| Added amount of NaOH [wt.-%/TDM] | 5 | 7 | 8 | 9 |
| Yield [wt.-%] | 93.9 | 92.3 | 92.6 | 84.5 |

The results show that even with quite low amounts of added base equivalents already very good yields of liberated oil can be realized without addition of organic solvents or salts like sodium chloride. Further it becomes clear that there is a ratio of added base equivalent to total dry matter, where a maximized yield can be realized. Further increasing the amount of base equivalents beyond that ratio do not increase the yield, but leads to even worse results in comparison to smaller amounts of added base equivalents. Best results were obtained with an amount of 12.5 to 20 moles NaOH per 10 kg of TDM.

Example 4: Influence of the Amount of Added Base Equivalents on the Liberation of the Oil To test the significance of the amount of added base equivalents on the efficiency of the oil liberation from the biomass, the effect of addition of different amounts of caustic soda to the biomass with respect to the liberation of oil was tested. The ratio of base equivalents added to total dry matter is depicted in table 3 as well as the amount of oil as set free by the addition of the caustic soda. All experiments were carried out with one liter of enzymatically treated and subsequently concentrated fermentation broth using a stirring vessel BIOSTAT® B-DCU-Quad 2L (Sartorius, Germany). The total dry matter of the samples was 30 wt.-%. Demulsification was carried out for 24 hours at a temperature of 80° C. The suspension was stirred with 300 rpm. Caustic soda was added continuously to avoid high pH values. After 24 hours the demulsified compositions were neutralized to pH 7.5. After neutralization, a 50 g sample of the homogenized suspension was taken and separation of the cell debris was carried out by centrifugation at 13500 g. Subsequently the amount of EPA and DHA in the supernatant was determined.

TABLE 3

Influence of the amount of added NaOH on the amount of liberated oil

|  | Added amount of NaOH [mol/10 kg TDM] | | | | |
| --- | --- | --- | --- | --- | --- |
|  | 10 | 12.5 | 15 | 17.5 | 20 |
| Added amount of NaOH [wt.-%/TDM] | 4 | 5 | 6 | 7 | 8 |
| Yield [wt.-%] | 92.5 | 94.0 | 95.2 | 95.2 | 93.8 |

The results show that even with quite low amounts of added base equivalents already very good yields of liberated oil can be realized without addition of organic solvents or salts like sodium chloride. Further it becomes clear that there is a ratio of added base equivalent to total dry matter, where a maximized yield can be realized. Further increasing the amount of base equivalents beyond that ratio do not increase the yield, but leads to even worse results in comparison to smaller amounts of added base equivalents. Best results were obtained with an amount of 12.5 to 17.5 moles NaOH per 10 kg of TDM.

Example 5: Influence of the Amount of Added Base Equivalents on the Liberation of the Oil To test the significance of the amount of added base equivalents on the efficiency of the oil liberation from the biomass, the effect of addition of different amounts of caustic soda to the biomass with respect to the liberation of oil was tested. The ratio of base equivalents added to total dry matter is depicted in table 4 as well as the amount of oil as set free by the addition of the caustic soda. All experiments were carried out with one liter of enzymatically treated and subsequently concentrated fermentation broth using a stirring vessel BIOSTAT® B-DCU-Quad 2L (Sartorius, Germany). The total dry matter of the samples was 35.5 wt.-%. Demulsification was carried out for 24 hours at a temperature of 80° C. The suspension was stirred with 300 rpm. Caustic soda was added continuously to avoid high pH values. After 24 hours the demulsified compositions were neutralized to pH 7.5. After neutralization, a 50 g sample of the homogenized suspension was taken and separation of the cell debris was carried out by centrifugation at 13500 g. Subsequently the amount of EPA and DHA in the supernatant was determined.

TABLE 4

Influence of the amount of added NaOH on the amount of liberated oil

|  | Added amount of NaOH [mol/10 kg TDM] | | | | |
| --- | --- | --- | --- | --- | --- |
|  | 10 | 12.5 | 15 | 17.5 | 20 |
| Added amount of NaOH [wt.-%/TDM] | 4 | 5 | 6 | 7 | 8 |
| Yield [wt.-%] | 88.5 | 91.8 | 91.0 | 89.0 | 87.0 |

The results show that even with quite low amounts of added base equivalents already very good yields of liberated oil can be realized without addition of organic solvents or salts like sodium chloride. Further it becomes clear that there is a ratio of added base equivalent to total dry matter, where a maximized yield can be realized. Further increasing the amount of base equivalents beyond that ratio do not increase the yield, but leads to even worse results in comparison to smaller amounts of added base equivalents. Best results were obtained with an amount of 12.5 to 15 moles NaOH per 10 kg of TDM.

Example 6: Influence of Temperature, Total Dry Matter, Amount of Caustic and Stirring Speed on the Liberation of the Oil To test the influence and interdependence of temperature, total dry matter content (TDM), amount of base equivalents and stirring speed on the liberation of the oil, tests were carried out with enzymatically treated fermentation broths which were concentrated by forced circulation evaporation to a total dry matter content of either 25, 30 or 35 wt.-%. Tests were carried out in a stirring vessel BIOSTAT® B-DCU-Quad 2L (Sartorius, Germany). The volume of the concentrated suspensions as used in the tests was 1 L for each sample. In the tests the total amount of base equivalent added was varied from 5 to 7 wt.-%, while the demulsification was carried out either at 70, 80 or 90° C. As base equivalent NaOH was added in liquid form (20 wt.-% NaOH solution) in one shot at the beginning of the demulsification step. Demulsification took place at a stirrer speed of either 100, 550 or 1000 rpm for 24 hours. After 24 hours the resulting compositions were neutralized by adding sulfuric acid. After neutralization, a 50 g sample of the homogenized suspension was taken and separation of the cell debris was carried out by centrifugation at 13500 g. Subsequently the amount of EPA and DHA in the supernatant was determined.

TABLE 5

Influence of temperature, TDM and stirring speed on the yield of liberated oil

| Temperature [° C.] | 70 | 70 | 90 | 90 | 70 | 70 | 90 | 90 | 80 | 80 |
|---|---|---|---|---|---|---|---|---|---|---|
| TDM [wt.-%] | 25 | 35 | 25 | 35 | 25 | 35 | 25 | 35 | 30 | 30 |
| Amount of NaOH [wt.-% per TDM] | 5 | 7 | 7 | 5 | 7 | 5 | 5 | 7 | 6 | 6 |
| Amount of NaOH [mol/10 kg TDM] | 12.5 | 17.5 | 17.5 | 12.5 | 17.5 | 12.5 | 12.5 | 17.5 | 15 | 15 |
| Stirrer speed [rpm] | 100 | 100 | 100 | 100 | 1000 | 1000 | 1000 | 1000 | 550 | 550 |
| Yield [wt.-%] | 90.3 | 96.2 | 82.9 | 95.5 | 76.6 | 93.1 | 93.1 | 90.0 | 94.9 | 93.9 |

As can be seen with a TDM of 35 wt.-% always very good results could be realized, i.e. an oil yield of at least 90 wt.-%, even at a rather high amount of base equivalents and a rather low temperature. On the contrary, at a TDM of only 25 wt.-%, the results might get significantly worse, when the amount of base equivalent is quite high, in particular when the temperature is quite low.

Example 7: Influence of Temperature on the Liberation of the Oil

To test the significance of the temperature on the liberation of the oil, tests were carried out with enzymatically treated fermentation broths which were concentrated by forced circulation evaporation to a total dry matter content of 33 wt.-%. Tests were carried out in a stirring vessel BIOSTAT® B-DCU-Quad 2L (Sartorius, Germany). The volume of the concentrated suspensions as used in the tests was 1 L for each sample. In each test the same total amount of base equivalent (6 wt.-% NaOH per TDM, i.e. 15 moles NaOH per 10 kg TDM) was added, while the demulsification was carried out either at 40, 50 or 90° C. The base equivalent was added in liquid form (20 wt.-% NaOH solution) in one shot at the beginning of the demulsification step. Demulsification took place at a stirrer speed of 300 rpm for 24 hours. After 24 hours the resulting composition was neutralized by adding sulfuric acid. After neutralization, a 50 g sample of the homogenized suspension was taken and separation of the cell debris was carried out by centrifugation at 13500 g. Subsequently the amount of EPA and DHA in the supernatant was determined.

TABLE 6

Influence of the temperature on the yield of liberated oil

| | Temperature [° C.] | | |
|---|---|---|---|
| | 40 | 50 | 90 |
| Yield [wt.-%] | 85.4 | 87.6 | 93.0 |

It turned out that even at low temperatures as like 40° C. or 50° C. a very efficient liberation of oil can be realized, when the appropriate amount of base equivalents is added.

Example 8: Demulsification at Very Low Temperatures

To further test the significance of the temperature on the liberation of the oil, tests were carried out with enzymatically treated fermentation broths which were concentrated by forced circulation evaporation to a total dry matter content of 33.5 wt.-%. Tests were carried out in a stirring vessel BIOSTAT® B-DCU-Quad 2L (Sartorius, Germany). The volume of the used concentrated suspensions was 1 L for each sample. In each test the same total amount of base equivalent (6 wt.-% NaOH per TDM, i.e. 15 moles NaOH per 10 kg TDM) was added, while the demulsification was carried out either at 30° C. or 40° C. The base equivalent was added in liquid form (20 wt.-% NaOH solution) in one shot at the beginning of the demulsification step. Demulsification took place at a stirrer speed of 300 rpm for 24 hours. After 24 hours the resulting composition was neutralized by adding sulfuric acid. After neutralization, a 50 g sample of the homogenized suspension was taken and separation of the cell debris was carried out by centrifugation at 13500 g. Subsequently the amount of EPA and DHA in the supernatant was determined.

TABLE 7

Influence of the temperature on the yield of liberated oil

| | Temperature [° C.] | |
|---|---|---|
| | 30 | 40 |
| Yield [wt.-%] | 85.8 | 84.6 |

It turned out that even at temperatures as low as 30° C. an efficient liberation of oil can be realized, when the appropriate amount of base equivalents is added.

Example 9: Influence of Demulsification Time on the Liberation of Oil

To test the significance of the exposure time on the liberation of the oil, tests were carried out with enzymatically treated fermentation broths which were concentrated by forced circulation evaporation to a total dry matter content of 36.2 wt.-%. Tests were carried out in a stirring vessel. The volume of the used concentrated suspensions was 300 L for each sample. In each test the same total amount of base equivalent (6 wt.-% NaOH per TDM, i.e. 15 moles NaOH per 10 kg TDM) was added and the temperature was kept at 80° C. The base equivalent was added stepwise in liquid form (20 wt.-% NaOH solution) in the course of the exposure, so that the pH of the suspension never exceeded pH 9.5. The exposure times were varied from 4 to 23 hours. After the incubation the resulting composition was neutralized by adding sulfuric acid. After neutralization, a 50 g sample of the homogenized suspension was taken and separation of the cell debris was carried out by centrifugation at 13500 g. Subsequently the amount of EPA and DHA in the supernatant was determined.

TABLE 8

Influence of the time of demulsification on the yield of liberated oil

| | Exposure time [h] | | | |
|---|---|---|---|---|
| | 4 | 9 | 13 | 23 |
| Yield [wt.-%] | 90.5 | 92.0 | 92.0 | 91.3 |

It turned out that surprisingly almost the same amount of oil could be isolated at exposure times varying from 4 to 23 hours. That means that quite short exposure times already lead to very good yields, so that longer, time and energy consuming incubation times can be avoided.

Example 10: Use of $Ca(OH)_2$ as Base in the Demulsification

Enzymatically treated fermentation broths were concentrated by forced circulation evaporation to a total dry matter content of 34 wt.-%. Tests were carried out in a stirring vessel BIOSTAT® B-DCU-Quad 2L (Sartorius, Germany). The volume of the used concentrated suspensions was one liter for each sample. The demulsification was carried out at a temperature of 80° C. and at an exposure time of 24 hours. The suspensions were stirred with 300 rpm. Either 10.6 moles base equivalents or 14.0 moles base equivalents of $Ca(OH)_2$ per 10 kg total dry matter were added to the suspension. $Ca(OH)_2$ was added stepwise in suspended form (20 wt.-% $Ca(OH)_2$ in water) in the course of the exposure, so that the pH value of the suspension never exceeded pH 9.5. After the incubation the resulting composition was neutralized by adding sulfuric acid. After neutralization, a 50 g sample of the homogenized suspension was taken and separation of the cell debris was carried out by centrifugation at 13500 g. Subsequently the amount of EPA and DHA in the supernatant was determined.

TABLE 9

Influence of the amount of added $Ca(OH)_2$ on the amount of liberated oil

| | Added amount of $Ca(OH)_2$ [mol/10 kg TDM] | |
|---|---|---|
| | 10.6 | 14.0 |
| Added amount of $Ca(OH)_2$ [wt.-%/TDM] | 3.9 | 5.2 |
| Added amount of $Ca(OH)_2$ [g] | 13.3 | 17.8 |
| Yield [wt.-%] | 90.2 | 90.1 |

As can be seen, increasing the amount of $Ca(OH)_2$ from 10.6 to 14.0 moles per 10 kg total dry matter has no influence on the yield of liberated oil. Addition of the same amount of base equivalents leads to similar good results as in case of NaOH.

Example 11: Demulsification without Enzymatic Treatment of the Cells

To test the significance of the enzymatic treatment of the cells on the liberation of the oil, tests were carried out with fermentation broths which after pasteurisation were not treated enzymatically, but directly concentrated by forced circulation evaporation to a total dry matter content of 32.8 wt.-%. Tests were carried out in a stirring vessel BIOSTAT® B-DCU-Quad 2L (Sartorius, Germany). The volume of the used concentrated suspensions was 1 L for each sample. In each test the same total amount of base equivalent (6 wt.-% NaOH per TDM, i.e. 15 moles NaOH per 10 kg TDM) was added, and the demulsification was carried out at 90° C. for 24 hours at a stirrer speed of 300 rpm. The base equivalent was added in liquid form (20 wt.-% NaOH solution) in one shot at the beginning of the demulsification step. After 24 hours the resulting composition was neutralized by adding sulfuric acid. After neutralization, a 50 g sample of the homogenized suspension was taken and separation of the cell debris was carried out by centrifugation at 13500 g. Subsequently the amount of EPA and DHA in the supernatant was determined.

It turned out that surprisingly even without prior enzymatic treatment of the cells quite good oil yields of about 80% could be realized, when an appropriate amount of total dry matter is provided and an appropriate amount of base equivalents is applied during demulsification.

The invention claimed is:

1. A method of isolating a polyunsaturated fatty acids (PUFAs) containing lipid from a biomass, comprising the following steps:
   a) providing a suspension of a biomass comprising cells which contain PUFAs containing lipid;
   b) optionally lysing the cells of the biomass;
   c) concentrating the suspension to a total dry matter (TDM) content of 20 to 60 wt %, if the suspension has a lower percentage TDM content;
   d) adjusting the suspension to a temperature of 20° C. to 100° C.;
   e) maintaining the temperature in the range in step d) for at least 1 hour, while adding 10 to 20 moles of base equivalent per 10 kg of total dry matter contained in the suspension;
   and wherein the isolation of said lipid does not include an extraction in which lipid is recovered from an organic solvent and is carried out without the addition of salt to the concentrated suspension of step c).

2. The method of claim 1, wherein, in step d) the temperature of the suspension is adjusted to from 25 to below 60° C.

3. The method of claim 1, wherein, in step d) the temperature of the suspension is adjusted to 60-90° C.

4. The method of claim 1, wherein, in step e), the temperature is maintained in the range of step d) for 1-36 hours while the pH is kept in the range of 7.5-11.5.

5. The method of claim 1, wherein 10 to 20 moles of base equivalent are added per 10 kg of total dry matter contained in the suspension and the pH is kept at 8.0-8.9.

6. The method of claim 1, wherein the base is a hydroxide, a carbonate or a bicarbonate.

7. The method of claim 1, wherein concentration of the suspension in step c) is carried out by evaporation of water at a temperature of not higher than 100° C.

8. The method of claim 1, wherein the suspension as provided in step a) already has a dry matter content of 20 to 60 wt %.

9. The method of claim 1, wherein the suspension is fermentation broth, and after step e) the pH is adjusted to 6.5-7.5.

10. The method of claim 9, wherein the suspension is fermentation broth, and cells are lysed in step b) without the addition of salt.

11. The method of claim 10, wherein lysing of the cells is carried out enzymatically, mechanically, chemically and/or physically.

12. The method of claim 11, wherein, in step d), the temperature of the suspension is adjusted to from 25 to below 60° C. and, in step e), the temperature is maintained in this range for 1-36 hours.

13. The method of claim 11, wherein, in step d), the temperature of the suspension is adjusted to 60-90° C., and, in step e) the temperature is maintained in this range for 1-36 hours while the pH is kept in the range of 7.5-11.5.

14. The method of claim 1, wherein, in step e), the temperature is maintained in the range of step d) for 1-36 hours while 11 to 18 moles of base equivalent are added per 10 kg of total dry matter contained in the suspension.

15. The method of claim 1, wherein steps d) and e) are carried out without prior lysing the cells of the biomass.

16. The method of claim 1, comprising as further step, harvesting the PUFAs containing lipid.

17. The method of claim 1, wherein harvesting comprises neutralization of a demulsified suspension and subsequent separation of a resulting oil-containing light phase from a heavy phase comprising water, salts, residual oil and cell debris.

18. The method of claim 1, wherein the suspension is provided as a fermentation broth with a biomass density of at least 80 g/l.

19. The method claim 1, wherein the cells which contain a PUFAs containing lipid are selected from algae, fungi, protists, bacteria, microalgae, plant cells, and mixtures thereof.

20. The method claim 1, wherein the cells which contain a PUFAs containing lipid are of the family of Thraustochytrids.

* * * * *